United States Patent
Kim et al.

(10) Patent No.: US 10,407,701 B2
(45) Date of Patent: Sep. 10, 2019

(54) METHOD FOR PREPARING (METH)ACRYLATE GROUP-CONTAINING BENZOPHENONE FOR OPTICAL ADHESIVE USE AND OPTICAL ADHESIVE COMPOSITION

(71) Applicant: LG Chem, Ltd., Seoul (KR)

(72) Inventors: Jang Soon Kim, Daejeon (KR); Kwang Su Seo, Daejeon (KR); Won Gu Choi, Daejeon (KR)

(73) Assignee: LG Chem, Ltd. (KR)

( * ) Notice: Subject to any disclaimer, the term of this patent is extended or adjusted under 35 U.S.C. 154(b) by 125 days.

(21) Appl. No.: 15/548,663

(22) PCT Filed: Feb. 21, 2017

(86) PCT No.: PCT/KR2017/001907
§ 371 (c)(1),
(2) Date: Aug. 3, 2017

(87) PCT Pub. No.: WO2017/146444
PCT Pub. Date: Aug. 31, 2017

(65) Prior Publication Data
US 2018/0119180 A1    May 3, 2018

(30) Foreign Application Priority Data
Feb. 26, 2016 (KR) .................... 10-2016-0023188

(51) Int. Cl.
*C12P 7/62* (2006.01)
*C07C 69/54* (2006.01)
*C09J 4/00* (2006.01)
*C09J 133/02* (2006.01)

(52) U.S. Cl.
CPC .............. *C12P 7/62* (2013.01); *C07C 69/54* (2013.01); *C09J 4/00* (2013.01); *C09J 133/02* (2013.01); *C12Y 301/01003* (2013.01)

(58) Field of Classification Search
CPC ..... C12P 7/62; C07C 69/54; C09J 4/00; C09J 133/02; C12Y 301/01003
See application file for complete search history.

(56) References Cited

U.S. PATENT DOCUMENTS

| 3,365,421 A | 1/1968 | Horton et al. |
| 2011/0196169 A1 | 8/2011 | Knebel et al. |
| 2015/0075698 A1 | 3/2015 | Lu et al. |

FOREIGN PATENT DOCUMENTS

| CA | 1340884 C | 1/2000 | |
| EP | 0346788 A1 | 12/1989 | |
| KR | 20110083159 A | 7/2011 | |
| KR | 20110094309 A | 8/2011 | |
| KR | 20150035542 A | 4/2015 | |
| WO | 2005059151 A2 | 6/2005 | |
| WO | WO-2005059151 A2 * | 6/2005 | ............... C12P 7/26 |

OTHER PUBLICATIONS

Search Report from International Application No. PCT/KR2017/001907, dated Jun. 14, 2017.
Van Der Meulen, Inge, et al., "Copolymers from Unsaturated Macrolactones: Toward the Design of Cross-Linked Biodegradable Polyesters." Biomacromolecules, Published Feb. 14, 2011, vol. 12, pp. 837-843.
Taiwanese Search Report for 106105667 dated Feb. 8, 2018.

* cited by examiner

*Primary Examiner* — John E Uselding
(74) *Attorney, Agent, or Firm* — Lerner, David, Littenberg, Krumholz & Mentlik, LLP

(57) ABSTRACT

The present invention relates to a method for preparing a (meth)acrylate group-containing benzophenone for an optical adhesive use, the method including: preparing a raw material composition by mixing a hydroxy group-containing benzophenone-based compound and a (meth)acrylate-based compound; and carrying out a reaction of the hydroxy group-containing benzophenone-based compound and the (meth)acrylate-based compound by introducing an enzyme catalyst into the raw material composition. Further, the present invention provides an optical adhesive composition including a (meth)acrylate group-containing benzophenone prepared by the preparation method and a derivative thereof.

9 Claims, No Drawings

METHOD FOR PREPARING (METH)ACRYLATE GROUP-CONTAINING BENZOPHENONE FOR OPTICAL ADHESIVE USE AND OPTICAL ADHESIVE COMPOSITION

CROSS-REFERENCE TO RELATED APPLICATIONS

This application is a national phase entry under § 371 of International Application No. PCT/KR2017/001907, filed Feb. 21, 2017, which claims priority to Korean Patent Application No. 10-2016-0023188 filed in the Korean Intellectual Property Office on Feb. 26, 2016, the entire contents of which are incorporated herein by reference.

TECHNICAL FIELD

The present invention relates to a method for preparing a (meth)acrylate group-containing benzophenone to be used for an optical adhesive use and an optical adhesive composition containing the (meth)acrylate group-containing benzophenone prepared by the same and a derivative thereof.

BACKGROUND ART

An adhesive applied to an optical device such as a display device may be specifically used for interlayer adhesion of a multilayered structure, or may be used to hermetically seal parts which require moisture resistance. As the adhesive, a photo-curable adhesive may be used, and the photo-curable adhesive may be prepared by making a composition in which a photo-curable oligomer, a photo-crosslinkable monomer, a photoinitiator, and other additives are mixed, and curing the composition by means of photo-energy such as ultraviolet rays. As a component included in the composition for an adhesive, a benzophenone-based compound may be used, and specifically, a benzophenone-based compound having a functional group capable of reacting by light irradiation may be used. Specifically, the functional group capable of reacting by light irradiation may be a (meth)acrylate group, and a benzophenone having a (meth)acrylate group may be prepared by introducing the (meth)acrylate group into a chemical structure of benzophenone.

As a method for preparing a benzophenone having the (meth)acrylate group, Korean Patent Application Laid-Open No. 10-2011-0094309 describes a method for reacting hydroxybenzophenones and (meth)acrylic anhydride in the presence of catalytic amounts of acid, and EP 0346788 describes a method for reacting isocyanatoalkyl (meth) acrylates and hydroxybenzophenones by using a basic catalyst.

These existing preparation methods include a process of reacting the aforementioned components under an acid catalyst or a base catalyst, and may cause a problem in that the acid catalyst or the base catalyst and by-products produced during the process of neutralizing the acid catalyst or the base catalyst cause corrosion. Therefore, when the methods are applied to an optical device, and the like, durability may deteriorate, and as a result, there is a need for a method for preventing such a concern.

DETAILED DESCRIPTION OF THE INVENTION

Technical Problem

The present invention provides a method for preparing a (meth)acrylate group-containing benzophenone suitable for being used as an adhesive of an optical device, the method capable of preparing the (meth)acrylate group-containing benzophenone with high efficiency under mild conditions.

Further, the present invention provides an optical adhesive composition including a (meth)acrylate group-containing benzophenone, which is prepared by the method so as not to include components causing corrosion as an adhesive composition applied to an optical device, and a derivative thereof.

Technical Solution

An exemplary embodiment of the present invention provides a method for preparing a (meth)acrylate group-containing benzophenone for an optical adhesive use, the method including: preparing a raw material composition by mixing a hydroxy group-containing benzophenone-based compound and a (meth)acrylate-based compound; and carrying out a reaction of the hydroxy group-containing benzophenone-based compound and the (meth)acrylate-based compound by introducing an enzyme catalyst into the raw material composition.

Another exemplary embodiment of the present invention provides an optical adhesive composition including a (meth)acrylate group-containing benzophenone prepared by the preparation method and a derivative thereof.

Advantageous Effects

By the method for preparing a (meth)acrylate group-containing benzophenone, it is possible to prepare a (meth)acrylate group-containing benzophenone suitable for being used for an optical adhesive use with high efficiency. Further, by the method for preparing a (meth)acrylate group-containing benzophenone, it is possible to prepare the (meth)acrylate group-containing benzophenone with high efficiency under mild conditions.

Further, the optical adhesive composition is applied to an optical device, and the like and does not cause corrosion, by including a (meth)acrylate group-containing benzophenone prepared by the preparation method and a derivative thereof, and may obtain an advantage in that excellent durability and reliability are imparted.

BEST MODE

The benefits and features of the present invention, and the methods of achieving the benefits and features will become apparent with reference to Examples to be described below. However, the present invention is not limited to the Examples to be disclosed below, but may be implemented in various other forms, and the present Examples are only provided for rendering the disclosure of the present invention complete and for fully representing the scope of the invention to a person with ordinary skill in the technical field to which the present invention pertains, and the present invention will be defined only by the scope of the claims. Throughout the specification, like reference numerals indicate like constituent elements.

An exemplary embodiment of the present invention provides a method for preparing a (meth)acrylate group-containing benzophenone for an optical adhesive use, the method including: preparing a raw material composition by mixing a hydroxy group-containing benzophenone-based compound and a (meth)acrylate-based compound; and carrying out a reaction of the hydroxy group-containing benzophenone-based compound and the (meth)acrylate-based compound by introducing an enzyme catalyst into the raw material composition.

In the present specification, the term '(meth)acrylate' refers to methacrylate or acrylate.

In the related art, methods for preparing a (meth)acrylate group-containing benzophenone generally include a process of carrying out a reaction under an acid catalyst or a base catalyst, and generate by-products such as (meth)acrylic acid during the process of neutralizing the acid catalyst or the base catalyst. When the (meth)acrylate group-containing benzophenone is applied to an optical adhesive, there is a problem in that these residual by-products cause corrosion of an optical device, and the like.

The preparation method according to the present invention does not use an acid catalyst or a base catalyst in order to solve these problems. Specifically, since the preparation method uses an enzyme catalyst, products may be prepared under mild conditions, and by-products such as (meth) acrylic acid may not be generated. Therefore, when the (meth)acrylate group-containing benzophenone prepared by the preparation method is applied as one component of an optical adhesive to an optical device, and the like, the (meth)acrylate group-containing benzophenone does not cause corrosion and may obtain an advantage in that durability is improved.

Specifically, the preparation method includes preparing a raw material composition by mixing a hydroxy group-containing benzophenone-based compound and a (meth) acrylate-based compound.

The hydroxy group-containing benzophenone-based compound is a reactant which provides a benzophenone structure of a product, and may include one selected from the group consisting of 2-hydroxybenzophenone, 3-hydroxybenzophenone, 4-hydroxybenzophenone, 2-hydroxymethylbenzophenone, 3-hydroxymethylbenzophenone, 4-hydroxymethylbenzophenone, 2-hydroxyethylbenzophenone, 3-hydroxyethylbenzophenone, 4-hydroxyethylbenzophenone, 3-(1-hydroxyethyl) benzophenone, 4-(1-hydroxyethyl)benzophenone, and a combination thereof.

For example, the hydroxy group-containing benzophenone-based compound may include 4-hydroxymethylbenzophenone, and in this case, the enzyme catalyst and the benzophenone-based compound may exhibit an advantageous reactivity in consideration of a steric hindrance, and furthermore, even when a reaction with the (meth)acrylate-based compound is carried out or the benzophenone-based compound is applied as one component of an optical adhesive, the benzophenone-based compound is spatially advantageous, and may contribute to forming an appropriate crosslinking structure when the optical adhesive is cured.

The (meth)acrylate-based compound is an ester compound, and is a reactant which provides a product with a (meth)acrylate group. Specifically, the (meth)acrylate-based compound may include one selected from the group consisting of vinyl(meth)acrylate, allyl(meth)acrylate, alkyl (meth)acrylate, cycloalkyl(meth)acrylate, and a combination thereof.

Specifically, the alkyl(meth)acrylate may be a (meth) acrylate including an alkyl group having 1 to 20 carbon atoms, and may include one selected from the group consisting of, for example, methyl(meth)acrylate, ethyl(meth) acrylate, propyl(meth)acrylate, butyl(meth)acrylate, pentyl (meth)acrylate, hexyl(meth)acrylate, ethylhexyl(meth) acrylate, heptyl(meth)acrylate, octyl(meth)acrylate, nonyl (meth)acrylate, decyl(meth)acrylate, lauryl(meth)acrylate, dodecyl(meth)acrylate, tetradecyl(meth)acrylate, hexadecyl (meth)acrylate, and a combination thereof.

Specifically, the cycloalkyl(meth)acrylate is an acrylate including a monocyclic or polycyclic alkyl group having 3 to 20 carbon atoms, and may include one selected from the group consisting of, for example, cyclopentyl(meth)acrylate, cyclohexyl(meth)acrylate, isobornyl(meth)acrylate, adamantyl(meth)acrylate, and a combination thereof.

For example, the (meth)acrylate-based compound may include vinyl(meth)acrylate, and in this case, it is possible to have an advantage in that a reaction rate of the hydroxy group-containing benzophenone-based compound and the (meth)acrylate-based compound is fast, and a product is prepared with high efficiency.

The raw material composition may include the (meth) acrylate-based compound in an amount of about 1 mol to about 1.5 mol based on 1 mol of the hydroxy group-containing benzophenone-based compound. The reactants is used at a molar ratio within the range, thereby obtaining a product at a high yield by a subsequent reaction.

The raw material composition may further include one selected from the group consisting of an antioxidant, a polymerization inhibitor, and a combination thereof.

Specifically, the antioxidant is for obtaining a structural stability effect of a product by capturing radicals produced by heat or oxygen, light, and the like to prevent a raw material from being oxidized, a phenol-based antioxidant, an amine-based oxidant, and the like are used, and the antioxidant may include, for example, a butylated hydroxytoluene-based antioxidant.

The antioxidant may be used in an amount of more than 0 part by weight and 1 part by weight or less and, for example, about 0.05 part by weight to about 0.5 part by weight, based on 100 parts by weight of the raw material composition.

Further, the polymerization inhibitor appropriately controls polymerization of acrylate by absorbing radicals produced by heat or light, and it is possible to obtain a stabilizing effect when a raw material is stored for a long period of time. For example, the polymerization inhibitor may include one selected from the group consisting of hydroquinone monomethyl ether, hydroquinone, phenothiazine, and a combination thereof.

The polymerization inhibitor may be used in an amount of more than 0 part by weight and 1 part by weight or less and, for example, about 0.05 part by weight to about 0.5 part by weight, based on 100 parts by weight of the raw material composition.

The preparation method includes carrying out a reaction of the hydroxy group-containing benzophenone-based compound and the (meth)acrylate-based compound by introducing an enzyme catalyst into the raw material composition.

The enzyme catalyst does not produce reaction by-products of acetaldehydes or alcohols, unlike an acid catalyst or a base catalyst, and may allow an optical adhesive, which is prepared by using the (meth)acrylate group-containing benzophenone prepared by the preparation method, to implement excellent durability.

Specifically, the enzyme catalyst may include lipase. The lipase is a triglyceride hydrolase, and may be extracted from the digestive organs of animals, or may be extracted from plants, microbes, or molds, and the like.

Specifically, the enzyme catalyst to be introduced for the reaction may include one selected from the group consisting of *Candida antarctica* B (CALB), *Candida antarctica* A (CALA), *Candida rugosa* lipase (CRL), Porcine pancreatic lipase (PPL), *Pseudomonas cepacia* lipase (PCL), *Rhizomucor miehei* lipase (RML), and a combination thereof.

For example, the enzyme catalyst may include *Candida antarctica* B (CALB), and in this case, the reaction efficiency of producing or exchanging esters is excellent as compared to other lipases, and the enzyme catalyst is immobilized on acrylic resin or epoxy-based resin particles with a micron size after the reaction, and thus is easily removed, and is better than other catalysts in that the enzyme catalyst can be re-used according to the reactivity.

The enzyme catalyst may be introduced in an amount of about 0.1 part by weight to about 10 parts by weight based on 100 parts by weight of the raw material composition. The enzyme catalyst is introduced in a content within the range to increase the reaction rate between the reactants, and can also be re-used and thus may obtain a product at a high yield as compared to the costs.

A reaction of the hydroxy group-containing benzophenone-based compound and the (meth)acrylate-based compound may be efficiently carried out by the enzyme catalyst.

The reaction may be carried out at about 30° C. to about 90° C., and for example, about 40° C. to about 60° C. When the reaction temperature is less than the range, there is a concern in that a reaction promoting action of the enzyme catalyst is minimal, and when the reaction temperature is more than the range, there is a concern in that the enzyme catalyst itself is damaged, and as a result, the reaction is not carried out.

Further, the reaction may be carried out at a temperature within the range for about 1 hour to about 24 hours and, for example, about 2 hours to about 6 hours. When the reaction time is less than the range, there is a concern in that the reaction does not sufficiently occur, and as a result, a yield of a product is reduced, and when the reaction time is more than the range, there is a concern in that the enzyme catalyst and the product are damaged or decomposed, and as a result, the yield is reduced.

The reaction of the hydroxy group-containing benzophenone-based compound and the (meth)acrylate-based compound may be carried out in the absence of a solvent. The reaction can be carried out in the presence or absence of a solvent. However, when the (meth)acrylate group-containing benzophenone produced by the reaction is used for an optical adhesive use, the (meth)acrylate group-containing benzophenone needs to be used after the solvent is completely removed. Therefore, the case where the reaction is carried out in the absence of a solvent may obtain an advantage in that a subsequent processing process for an optical adhesive use is rapidly carried out, and may be advantageous in terms of enhancing a function of an adhesive by minimizing unnecessary by-products of an optical adhesive.

The (meth)acrylate-based compound may be in the form of a liquid. When the (meth)acrylate-based compound is a liquid, it is possible to allow the raw material composition to have an appropriate viscosity, and accordingly, it is possible to obtain an advantage in that the reaction is easily carried out in the absence of a solvent.

The preparation method may further include a filtering step of removing the enzyme catalyst; and a purifying step, followed by the above-described steps.

The filtering step of removing the enzyme catalyst may be carried out by using a filter with about 100 mesh to about 300 mesh, and accordingly, it is possible to obtain an advantage in that the enzyme catalyst can be recycled at a high ratio.

Furthermore, the purifying step is a step for removing reaction by-products, and may be carried out by using distilled water.

Another exemplary embodiment of the present invention provides an optical adhesive composition including a (meth)acrylate group-containing benzophenone prepared by the preparation method and a derivative thereof.

The optical adhesive composition may be a photo-curable adhesive composition, and may exhibit excellent photo-curing efficiency by including a (meth)acrylate group-containing benzophenone prepared by the preparation method and a derivative thereof.

The (meth)acrylate group-containing benzophenone is in the form of a monomer, and the derivative of the (meth)acrylate group-containing benzophenone may include one selected from the group consisting of an oligomer, a prepolymer, a polymer, and a copolymer of the (meth)acrylate group-containing benzophenone, and a combination thereof.

That is, the optical adhesive composition may include one form selected from a monomer, an oligomer, a prepolymer, a polymer, and a copolymer of the (meth)acrylate group-containing benzophenone, or a combination thereof. The oligomer and the prepolymers are a polymer having a lower degree of polymerization than those of the polymer and the copolymer, and the prepolymer is a polymer having a higher degree of polymerization than that of the oligomer.

The optical adhesive composition includes the (meth)acrylate group-containing benzophenone prepared by the preparation method and a derivative thereof, and as a result, when the optical adhesive composition is used for an optical device, and the like, photo stability may be excellent, and excellent durability may be imparted.

Hereinafter, specific examples of the present invention will be suggested. However, the Examples described below are only provided for specifically exemplifying or explaining the present invention, and the present invention is not limited thereby.

EXAMPLES AND COMPARATIVE EXAMPLES

TABLE 1

| | Reactant | | Catalyst |
|---|---|---|---|
| Example 1 | 4-hydroxymethylbenzophenone | Vinyl acrylate | CALB |
| Example 2 | 4-hydroxymethylbenzophenone | Vinyl methacrylate | CALB |
| Example 3 | 4-hydroxymethylbenzophenone | Ethylhexyl acrylate | CALB |
| Example 4 | 4-hydroxymethylbenzophenone | Vinyl acrylate | PCL |
| Comparative Example 1 | 4-hydroxymethylbenzophenone | Acryloyl chloride | Triethylamine |
| Comparative Example 2 | 4-hydroxymethylbenzophenone | Methacrylic anhydride | Concentrated sulfuric acid |

Example 1

A raw material composition was prepared by mixing 4-hydroxymethylbenzophenone and vinyl acrylate at a molar ratio of 1:1.2, and based on 100 parts by weight of the raw material composition, 0.05 part by weight of butylated hydroxytoluene (BHT, Acros Organics) being an antioxidant and 0.05 part by weight of hydroquinone monomethyl ether (HQMME, Aldrich Chemicals Co., Ltd.) being a polymerization inhibitor were mixed. Based on 100 parts by weight of the raw material composition, 1 part by weight of *Candida antarctica* B (CALB) was introduced thereinto, and the resulting mixture was reacted under the conditions of the absence of a solvent and a temperature of 60° C. for 8 hours. After the reaction was completed, an enzyme catalyst was removed through a 200-mesh filter, and then the resulting product was subjected to a purification process three times by using distilled water, and then dried in an oven at 50° C. for 3 days. A white solid benzophenone acrylate was prepared by the above-described process.

Example 2

A raw material composition was prepared by mixing 4-hydroxymethylbenzophenone and vinyl methacrylate at a molar ratio of 1:1.2, and based on 100 parts by weight of the raw material composition, 0.05 part by weight of butylated hydroxytoluene (BHT, Acros Organics) being an antioxidant and 0.05 part by weight of hydroquinone monomethyl ether (HQMME, Aldrich Chemicals Co., Ltd.) being a polymerization inhibitor were mixed. Based on 100 parts by weight of the raw material composition, 1 part by weight of *Candida antarctica* B (CALB) was introduced thereinto, and the resulting mixture was reacted under the conditions of the absence of a solvent and a temperature of 60° C. for 8 hours. After the reaction was completed, an enzyme catalyst was removed through a 200-mesh filter, and then the resulting product was subjected to a purification process three times by using distilled water, and then dried in an oven at 50° C. for 3 days. A white solid benzophenone methacrylate was prepared by the above-described process.

Example 3

A raw material composition was prepared by mixing 4-hydroxybenzophenone and ethylhexyl acrylate at a molar ratio of 1:1.5, and based on 100 parts by weight of the raw material composition, 0.05 part by weight of butylated hydroxytoluene (BHT, Acros Organics) being an antioxidant and 0.05 part by weight of hydroquinone monomethyl ether (HQMME, Aldrich Chemicals Co., Ltd.) being a polymerization inhibitor were mixed. Based on 100 parts by weight of the raw material composition, 1 part by weight of *Candida antarctica* B (CALB) was introduced thereinto, and the resulting mixture was reacted under the conditions of the absence of a solvent, a temperature of 90° C., and vacuum ($9 \times 10^{-1}$ Pa) for 8 hours. After the reaction was completed, an enzyme catalyst was removed through a 200-mesh filter, and then the resulting product was subjected to a purification process three times by using distilled water, and then dried in an oven at 50° C. for 3 days. A white solid benzophenone acrylate was prepared by the above-described process.

Example 4

A raw material composition was prepared by mixing 4-hydroxymethylbenzophenone and vinyl acrylate at a molar ratio of 1:1.2. Based on 100 parts by weight of the raw material composition, 0.05 part by weight of butylated hydroxytoluene (BHT, Acros Organics) being an antioxidant and 0.05 part by weight of hydroquinone monomethyl ether (HQMME, Aldrich Chemicals Co., Ltd.) being a polymerization inhibitor were mixed. Based on 100 parts by weight of the raw material composition, 1 part by weight of *Pseudomonas cepacia* lipase was introduced thereinto, and the resulting mixture was reacted under the conditions of the absence of a solvent and a temperature of 60° C. for 8 hours. After the reaction was completed, an enzyme catalyst was removed through a 200-mesh filter, and then the resulting product was subjected to a purification process three times by using distilled water, and then dried in an oven at 50° C. for 3 days. A white solid benzophenone acrylate was prepared by the above-described process.

Comparative Example 1

A white solid benzophenone acrylate was prepared by introducing triethylamine as a base catalyst into a raw material composition including 4-hydroxymethylbenzophenone and acryloyl chloride to react the raw material composition.

Comparative Example 2

A white solid benzophenone methacrylate was prepared by introducing concentrated sulfuric acid as an acid catalyst into a raw material composition including 4-hydroxymethylbenzophenone and methacrylic anhydride to react the raw material composition.

<Evaluation>

Experimental Example 1: Measurement of Purity

For Examples 1 to 4 and Comparative Examples 1 and 2, a yield of converting each of the reactants into a benzophenone product having a (meth)acrylate group was measured, and is shown in the following Table 2. A purity was analyzed by comparing GCMS chromatogram areas. The sample was dissolved in methanol at a mass ratio of 1:200, and was subjected to analysis through GCMS.
Injector: 300° C., 1.0 mL/min He, 10:1 s/s ratio
Detector: 300° C.
Column: Agilent 19091S-433 (30 m×0.25 mm×0.25 μm)

TABLE 2

| | Yield (%) |
|---|---|
| Example 1 | 99 |
| Example 2 | 99 |
| Example 3 | 97 |
| Example 4 | 98 |
| Comparative Example 1 | 76 |
| Comparative Example 2 | 95 |

Referring to the results in Table 2, it could be seen that the benzophenone (meth)acrylates prepared by the preparation methods in Examples 1 to 4 had a yield of more than about 95%, for example, about 97% or more, and the yields higher than those of the preparation methods in Comparative Examples 1 and 2 were obtained.

The invention claimed is:
1. A method for preparing a (meth)acrylate group-containing benzophenone for an optical adhesive use, the method comprising:
preparing a raw material composition by mixing a hydroxy group-containing benzophenone-based compound and a (meth)acrylate-based compound; and
carrying out a reaction of the hydroxy group-containing benzophenone-based compound and the (meth)acrylate-based compound by introducing an enzyme catalyst into the raw material composition,
wherein the hydroxy group-containing benzophenone-based compound comprises one selected from the group consisting of 2-hydroxybenzophenone, 3-hy- droxybenzophenone, 4-hydroxybenzophenone, 2-hydroxymethylbenzophenone, 3-hydroxymethylbenzophenone, 4-hydroxymethylbenzophenone, 2-hydroxyethylbenzophenone, 3-hydroxyethylbenzophenone, 4-hydroxyethylbenzophenone, 3-(1-hydroxyethyl)benzophenone, 4-(1-hydroxyethyl)benzophenone, and a combination thereof, and wherein the raw material composition further includes one selected from the group consisting of an antioxidant, a polymerization inhibitor, and a combination thereof.

2. The method of claim 1, wherein the (meth)acrylate-based compound comprises one selected from the group consisting of vinyl(meth)acrylate, allyl(meth)acrylate, alkyl (meth)acrylate, cycloalkyl(meth)acrylate, and a combination thereof.

3. The method of claim 1, wherein the enzyme catalyst comprises lipase.

4. The method of claim 3, wherein the enzyme catalyst comprises one selected from the group consisting of *Candida antarctica* B (CALB), *Candida antarctica* A (CALA), *Candida rugosa* lipase (CRL), Porcine pancreatic lipase (PPL), *Pseudomonas cepacia* lipase (PCL), *Rhizomucor miehei* lipase (RML), and a combination thereof.

5. The method of claim 1, wherein the raw material composition comprises the (meth)acrylate-based compound in an amount of 1 mol to 1.5 mol based on 1 mol of the hydroxy group-containing benzophenone-based compound.

6. The method of claim 1, wherein the enzyme catalyst is introduced in an amount of 0.1 part by weight to 10 parts by weight based on 100 parts by weight of the raw material composition.

7. The method of claim 1, wherein the reaction is carried out at 30° C. to 90° C.

8. The method of claim 7, wherein the reaction is carried out for 1 hour to 24 hours.

9. The method of claim 1, wherein the reaction is carried out in the absence of a solvent other than the (meth)acrylate-based compound.

\* \* \* \* \*